United States Patent [19]

Gill et al.

[11] Patent Number: 4,904,468

[45] Date of Patent: Feb. 27, 1990

[54] CANINE CORONAVIRUS VACCINE

[75] Inventors: Michael A. Gill; Stephen W. May, both of Lincoln, Nebr.

[73] Assignee: Norden Laboratories, Inc., Lincoln, Nebr.

[21] Appl. No.: 59,437

[22] Filed: Jun. 8, 1987

[51] Int. Cl.$^4$ .......................... A61K 39/12; C12N 7/00
[52] U.S. Cl. ...................................... 424/89; 435/235; 435/236; 435/237; 435/238; 435/239
[58] Field of Search .................. 424/89; 435/235–239

[56] References Cited

U.S. PATENT DOCUMENTS 4,567,042 1/1986 Acree et al. ........................ 424/89
4,567,043 1/1986 Acree et al. ........................ 424/89

FOREIGN PATENT DOCUMENTS

WO85/00014 1/1985 PCT Int'l Appl.
WO86/05806 10/1986 PCT Int'l Appl.

OTHER PUBLICATIONS

Siddel et al., "The Structure and Replication of Corona Virus", Current Topics in Microbiology and Immunology 99:141 (1982).
Morein et al., *Vaccine* 3:83 (1985).
Delmas et al., *J. Gen. Virol.* 67, 1405–1418 (1986).
Jimenez et al., *Journal of Virology*, vol. 60, No. 1, Oct. 1986, pp. 131–139.
Niesters et al., *Virus Res.* 5: 253 (1986).

*Primary Examiner*—Margaret Moskowitz
*Assistant Examiner*—Abdel Mohamed
*Attorney, Agent, or Firm*—Edward T. Lentz; Alan D. Lourie

[57] ABSTRACT

A vaccine for protecting canine animals from disease caused by infection with canine corona virus (CCV) which comprises an effective amount of the cell-associated CCV peplomer protein. A polyvalent vaccine comprising an effective amount of cell-associated CCV peplomer protein and an effective amount of an antigenic component which is protective against one or more additional pathogenic organisms or viruses are also disclosed.

13 Claims, No Drawings

CANINE CORONAVIRUS VACCINE

FIELD OF THE INVENTION

This invention relates to veterinary vaccines and, in particular, to a vaccine for protecting canine animals from infection by Canine Coronavirus.

BACKGROUND INFORMATION

Coronaviruses are among the most important causative agents of several diseases including encephalitis, hepatitis, pneumonitis, neasopharyngitis, peritonitis, and gastroenteritis in a wide variety of animal species. With respect to enteric infections, coronaviruses have been detected in the feces of man, pigs, calves, mice, rats, chickens, turkeys, dogs, cats and horses.

Canine coronavirus (CCV) enteritis was first reported in 1974 by Binn, et al., *Proc. 78th Ann. Mtg.. U.S. Anim. Health Assoc. Roanoke VA Oct:*359–366 (1974). The virus was isolated initially in 1971 from military dogs suffering from suspected viral gastroenteritis.

For reasons which are as yet unclear, in the late 1970's coronaviral enteritis emerged as a significant disease of dogs. The primary source of infection appears to be fecal material from infected animals. Oral infection leads to replication in the epithelial cells of the small intestine. Virus generally can be isolated from the feces of infected dogs between 3 and 14 days post-inoculation.

CCV gastroenteritis is characterized by mild depression, anorexia and loose stool with an especially offensive odor. The onset of illness is often sudden with diarrhea accompanied or shortly preceded by vomiting. Vomiting usually decreases in frequency after the first day or two of illness. The feces often contains mucous and variable amounts of blood, giving it an orange in red tint. Projectile diarrhea sometimes is seen either as a watery or bloody fluid. Young pups may become rapidly dehydrated even though fluid therapy is instituted early in the course of the illness. Deaths have occurred within as little as 24 to 36 hours after onset of clinical signs despite good supportive care. Stress seems to increase the severity of the disease. Elevated body temperatures have been observed in some cases, but most animals tend to be afebrile, and in some affected dogs, temperatures can be distinctly subnormal. See, Carmichael, "Infectious canine enteritis caused by a corona like virus," Laboratory Report, The James A. Baker Institute for Animal Health, Cornell U. 2(9) (1978).

Most affected dogs recover after week to 10 days, but dogs given early symptomatic treatment and kept warm and quiet sometimes recover more rapidly. Appel et al., *Cornell Vet.* 69:123–133 (1979). A persistent diarrhea for 3 to 4 weeks, that was refractory to treatment, has been reported in several instances. Appel et al., *Canine Prac.* 7:22–36 (1980). Concurrent ocular and nasal discharges have been noted, but their relationship to the primary infection is not known. Morphological lesions in CCV enteritis are restricted to the intestine and mesenteric lymph nodes. Histological changes are remarkably similar to those described in gnotobiotic calves infected with bovine coronavirus. Uncomplicated infection in experimental dogs is mild, and pathological changes are either not detectable or consist of dilated intestinal loops filled with watery, green-yellow fecal material. The mesenteric lymph nodes are commonly enlarged and congested or hemorrhagic.

In one case, the incubation period in experimentally infected dogs was about 24 to 36 hours. The dogs did not exhibit the typical clinical symptoms or the classic diarrhea associated with coronavirus gastroenteritis. Microscopic changes were modest, characterized by atrophy of the intestinal villi and deepening of crypts, increase in cellularity of the lamina propria, flattening of epithelial cells, and discharge of goblet cells. Keenan et al., *Am. J. Vet. Res.* 37:247–256 (1976). The mild symptoms may be due to the isolation procedures used for inoculatinq the experimentally infected dogs, and to the fact that the dogs were free from other major pathogens and parasites.

Specific treatment of CCV enteritis is not available. Therapy is supportive with attempts to replace fluid and electrolyte losses, control diarrhea and prevent or control secondary bacterial infections.

Serum antibody titers in dogs inoculated parenterally with CCV were higher than in orally exposed dogs. After oral challenge, the dogs responded with an anamnestic-type antibody response and shed virus for a shorter period of time than nonexposed control dogs. It appeared that local immunity, possibly mediated by IgA antibodies in the intestine, was essential for protection against CCV infection, in a manner similar to transmissible gastroenteritis in pigs. Appel et al., *Canine Prac.* 7:22–36 (1980).

Presumptive diagnosis of CCV enteritis is based upon clinical signs. Other causes of acute emesis and diarrhea in dogs which might also be considered include intoxications, bacterial enteritis, coccidiosis, acute pancreatitis, acute renal or hepatic failure, and other viral infections. Evidence of rapid spread is strongly suggestive of CCV enteritis. There have been several reports describing electron microscopic detection of canine parvovirus in association with CCV particles in canine fecal specimens. See, for example, Carmichael, cited above; Evermann et al., *J. Am. Vet. Med. Ass.* 177:784–786 (1980); Reseto et al., *Arch. Virol.* 66:89–93 (1980). One report detected, in addition, a canine rotavirus in one fecal specimen. McNulty et al., *Vet. Res.* 106:350–351 (1980). This indicates that the severity of field cases may be attributed, in part, to multiple viral infections.

Isolation of CCV from fecal specimens or intestinal contents has been reported by several investigators with some difficulties. Because of their fastidious nature and lack of susceptible cellular substrates, coronaviruses are often not isolated or diagnosed. Seroconversion or post mortem findings in fatal cases, including immunofluorescence of frozen intestinal sections all can be used for a proper etiologic diagnosis.

Coronaviruses are large (about 100 nm in diameter), enveloped, RNA viruses having a helical nucleocapsid with characteristic large club-shaped projections, or spikes, referred to as peplomers. The RNA comprises a single, linear single strand, with positive polarity, of roughly $5.5 \times 10^6$ daltons. In ultrathin tissue sections, the virus appears, by electron microscopy, to form by budding into vacuoles in the cytoplasm. The virus is antigenically related to the Swine Transmissible Gastroenteritis Virus.

Acree et al., U.S. Pat. No. 4,567,042 and U.S. Pat. No. 4,567,043, describe an inactivated and an attenuated canine coronavirus vaccine, respectively, both comprising spent fluid medium.

SUMMARY OF THE INVENTION

The invention is a vaccine for protecting canine animals from disease caused by infection with Canine Coronavirus (CCV) which comprises an effective amount of the cell-associated CCV peplomer protein.

The invention is also a process for preparing such vaccine which comprises:

a. infecting a cell culture with a Multiplicity of Infection (MOI) of CCV of at least 0.2;
b. culturing the cells for 6–18 hours;
c. discarding the spent fluid medium;
d. disrupting the cells;
e. collecting the cell-associated peplomer protein from the disrupted cells; and,
f. combining the cell-associated peplomer with a parenterally acceptable carrier.

Another aspect of the invention is a polyvalent vaccine comprising an effective amount of cell-associated CCV peplomer protein and an effective amount of an antigenic component which is protective against one or more additional pathogenic organisms or viruses.

Another aspect of the invention is a method of protecting a canine animal against disease caused by CCV infection which comprises parenterally administering to the animal the vaccine of the invention.

DETAILED DESCRIPTION OF THE INVENTION

CCV replicates intracellularly post-infection. In the course of the replication cycle, CCV RNA is translated to produce various structural and non structural proteins involved in viral replication. Capsid proteins including the peplomer, or E2, protein appear to be translated on membrane bound polyribosomes at the rough endoplasmic reticulum. In the course of viral maturation, cytoplasmic nucleocapsids bud into the endoplasmic reticulum, picking up the capsid proteins to form mature virus particles and are then externalized through the Golgi apparatus. The peplomer protein may undergo cleavage or other post-translational modification subsequent to particle formation. Coincidentally, some peplomer proteins appear to remain embedded in the lipid bilayer of the cell membrane upon initial entry into the infected cell.

It has now been discovered that the cell-associated peplomer protein, that is, the peplomer protein as it exists in the infected cell prior to particle formation, induces an immune response upon parenteral administration in a canine animal which response is protective against disease symptoms normally associated with infection by virulent CCV. This discovery is surprising in view of the fact that whole virus, attenuated or inactivated, is relatively poorly immunoprotective.

The cell associated peplomer protein (about 203,000 MW) can be produced by appropriate culture and harvest of infected cells, by synthesis or by genetic engineering. To produce the peplomer by cell culture, a susceptible cell culture is infected with the virus and cultured. Any primary or continuous cell culture capable of supporting replication of the virus or in which the virus can be adapted to replicate can be used. Examples are primary canine cells such as canine kidney cells and canine thymus cells; canine cells lines such as the Madin Darby Canine Kidney cell line and the A-72 fibroblastic canine cell line (ATCC CRL 1542); primary feline cells such as primary feline kidney cells; feline cells lines such as the Crandall Feline Kidney cell line and Wood's Feline cell line; and other primary or continuous mammalian cells such as the Vero Monkey Kidney cell line.

The virus can be isolated from clinical infections by known techniques. Such techniques include suspending fecal matter from an infected animal, such as in a tissue culture medium, in the presence of a polycation and then inoculating a primary cell culture with a supernatant therefrom. See, for example, Binn et al., *Proc. 78th Ann. Mtg.. U.S. Anim. Health Assoc., Roanoke VA Oct.*:3-59–366 (1974), Keenan et al. et al., *Am. J. Vet. Res.* 37:247–256 (1976) and Tingpalapong et al., *Am.. J. Vet. Res.* 43:1687–1690 (1982). A virulent isolate, the I-71 strain originally isolated by Binn et al. in 1971, is among others that are publicly available. It can be obtained, for example, from the American Type Culture Collection in Rockville, Maryland, U.S.A. under accession number VR 809. Other isolates include K-378, S-378, A76- 5 and ATCC VR 2068, referred to by Acree et al. in U.S. Pat. No. 4,567,042 and U.S. Pat. No. 4,567,043.

To produce and harvest the cell associated peplomer antigen, the cell culture is infected with 0.2 to 2.0 virus particles per cell, i.e., a Multiplicity of Infection (MOI) equal to 0.2 to 2.0, and preferably with an MOI of 0.4 to 1.5. Infected cells are cultured for about 6 to 18 hours, preferably 9 to 16 hours and most preferably 9 to 12 hours, post infection. The growth medium is then removed and the peplomer is harvested from the cells. This is preferably accomplished by replacing the spent fluid medium with a fresh fluid medium then disrupting the cells to release the cell-associated peplomer which is collected in the fresh fluid medium. The cell-associated peplomer is combined with a parenterally acceptable diluent or carrier for vaccine preparation. Conveniently, these steps can be combined by replacing the spent fluid medium with one which is parenterally tolerated prior to disruption.

Disruption can be accomplished by, e.g., mechanical, ultrasonic or chemical means, or by a combination thereof. It is conveniently accomplished by freezing the cells to about $-40$ to about $-70°$C. Upon thawing, the fluid, which contains the cell-associated peplomer, is collected. Because the medium in which the infected cell culture was grown has been discarded, the fresh fluid medium is substantially free of extracellular virus which had been externalized during growth of the infected cell culture. However, the fluid should be treated to inactivate residual, extracellular and intracellular viruses and nucleocapsids, which intracellular particles and nucleocapsids are released upon disruption. Any standard virus inactivation procedure can be employed, as long as the peplomer is not denatured. Such techniques include irradiation and chemical inactivation such as by addition of binary ethyleneimine, beta propiolactone, formaldehyde, phenol or acetyl ethyleneimine. Stabilizers, adjuvants buffering agents and/or preservatives which are parenterally tolerated can also be added to prepare the final vaccine formulation. For example, the preferred vaccine comprises menthiolate, e.g., 1:60,000, and ethylene mateic anhydride adjuvant, e.g., 0.2%.

In preparing the vaccine of the invention by cell culture, it is important, contrary to prior reports of CCV vaccine preparation, to remove the spent fluid medium from the cells prior to disruption. Although the reason is not clear, vaccines prepared as described above but using the spent medium rather than a fresh fluid produced lower virus neutralizing antibody titers than a vaccine containing fresh medium. Table 1, below, shows the virus neutralizing antibody titer in puppies of a vaccine prepared using spent medium and cells ("Fluid Vaccine") compared to a vaccine prepared in substantially the same manner except that the spent medium was decanted and replaced in accordance with this invention ("Cell Vaccine").

TABLE 1

Potency of Cell and Spent Fluid Vaccines in Puppies

| Group | Puppy No. | Virus Neutralizing Antibody Titer | |
|---|---|---|---|
| | | Pre second vacc. | Post second vacc. |
| Cell Vaccine | DE-70 | 32 | 128 |
| | DE-74 | 64 | 128 |
| | DE-76 | 16 | 64 |
| | DE-86 | 32 | 128 |
| Geometric Mean Titer | | 32 | 108 |
| Fluid Vaccine | DE-78 | 0 | 0 |
| | DE-80 | 0 | 0 |
| | DE-82 | 0 | 0 |
| | DE-84 | 0 | 0 |
| Geometric Mean Titer | | — | — |

The virus neutralizing antibody titers of the puppies show that the Cell Vaccine stimulated a protective immunological response (Geometric Mean Titer of 32) by the time of the second vaccination. By the time of the post-vaccination sampling, the response increased to a Geometric Mean Titer of 108. In contrast, puppies vaccinated with the Fluid vaccine remained negative throughout the testing period. This is a surprising result inasmuch as the spent medium contains CCV virus which would be expected to contribute to immunoprotection.

In an experiment designed to show the importance of time post infection to production of cell-associated peplomer antigen the amount of the protein which was cell-associated and the amount which was in the cell culture medium and therefore virus associated were determined hourly by an enzyme linked immunoassay (ELISA). The relative amounts of the antigen are shown in Table 2. Although not intending to be bound to a particular mechanism or explanation, it appears that the length of time for which cells are cultured is important because of changes which occur to the peplomer later in the infection cycle.

TABLE 2

| Hours Post-infection | Peplomer Protein | |
|---|---|---|
| | Cell-associated | Virus-associated |
| 11 | 4830 | 475 |
| 12 | 3895 | 556 |
| 13 | 5946 | 748 |
| 14 | 7282 | 1454 |
| 15 | 4423 | 2044 |

The amount of cell-associated peplomer antigen was also found to be dependent on the MOI. Table 3 shows data from a series of experiments in which the MOI ranged from 0.01 to 1.1. all cultures were harvested at 12 hours post-infection and the amount of the antigen was determined by ELISA.

TABLE 3

| MOI | Peplomer Protein | |
|---|---|---|
| | Cell-associated | Virus-associated |
| 0.01 | 1221 | 0 |
| 0.04 | 2911 | 13 |
| 0.1 | 3805 | 93 |
| 0.4 | 7877 | 207 |

TABLE 3-continued

| MOI | Peplomer Protein | |
|---|---|---|
| | Cell-associated | Virus-associated |
| 1.1 | 8927 | 646 |

The cell-associated peplomer antigen can be prepared by alternative procedures. For example, the peplomer can be purified such as by immunoaffinity adsorption chromatography, sequenced and then prepared by peptide synthesis or by expression in a recombinant host microorganism or cell of a DNA coding sequence derived from the peptide sequence. Furthermore, derivatives of the peplomer which retain the immunoprotective properties of the cell derived antigen can be prepared by standard recombinant DNA, protein engineering or chemical techniques.

However prepared, the vaccine is administered parenterally, for example, intramuscularly or subcutaneously, to dogs preferably of at least 3 months of age. A second dose 2 to 4 weeks after the first administration preferably is administered. Annual revaccination is recommended. If younger dogs are vaccinated, they are preferably revaccinated at 3 months of age. Vaccination of pregnant females is probably best avoided.

Each vaccine dose contains an effective amount of the cell-associated peplomer, i.e., an amount which is effective upon parenteral dual vaccinations in protecting canine animals against development of severe disease symptoms, i.e., gastroenteritis, caused by CCV infection. By following the above described procedure for producing the antigen by infection of a cell culture, a fluid will be obtained which contains an effective amount. Such fluid typically can be diluted by as much as 1/10 and still contain an effective amount. The total volume of each vaccine dose typically is 0.5 to 2 ml, preferably 1 to 1.5 ml.

The vaccine of the invention can also be combined with other vaccinal agents in a polyvalent vaccine, for example, in combination with other inactivated (killed) or attenuated canine viruses. Preferably, such other vaccinal component is another enteric disease causing virus, such as Rotavirus or Parvovirus, or other immunoprotective antigens derived therefrom. Many such inactivated and attenuated virus vaccines and antigens are known. A preferred polyvalent vaccine is a bivalent vaccine comprising a combination of the vaccine of the invention and a modified live or killed Parvovirus. Such vaccine comprises vaccinal amounts of the cell associated peplomer of the invention and of the modified live or killed Parvovirus (e.g., 6.3 $\text{Log}_{10}$ $\text{TCID}_{50}$ per dose). The total dose volume is 0.5 to 2 ml, preferably 1 to 1.5 ml. Carmichael et al., U.S. Pat. No. 4,303,645, disclose a modified live Canine Parvovirus vaccine, including the preparation of the vaccinal strain and effective doses thereof, which can be combined with the vaccine of the invention to prepare a bivalent vaccine of the invention.

The Examples which follow are illustrative of the invention but are not limiting.

EXAMPLE 1

Vaccine Preparation

Canine Coronavirus, strain NL-18, was isolated from a fecal specimen from a group of dogs suffering acute gastroenteritis. Initial isolation on primary canine kidney cells required 50 ug of diethyaminoethyl (DEAE)-dextran per ml of maintenance medium (basal medium Eagle (BME) with Earle's salts) (Grand Island Bioloqical Co., Grand Island, New York). DEAE-dextran was not required for additional passages. The virus was adapted to cell culture by 4 passaqes in the primary canine kidney cells and an additional 36 passages in a feline kidney cell line used at the 73d to 93d passaqe levels. Gill, "Isolation and Characterization of a Coronavirus," Doctoral Dissertation, University of Nebraska, August 1982, describes the isolation of CCV strain NL-18, previously referred to as strain CCV-18.

For inoculation of roller bottle cultures with virus, the medium from a tight monolayer of the feline kidney cell line cells is decanted. The medium is replaced with the maintenance medium, supplemented with 4–8% Polybrene (Siqma Chemical Co., St. Louis, Miss.), containing 2–10% virus which contains an undiluted virus titer of at least $10^{7.0}$ $TCID_{50}$/ml (0.2–1.0 MOI). Inoculated cultures are incubated for 9–16 hours at 35–37° C. Infection is manifested by the typical cytopathic effect (CPE) on cell monolayer, namely, patches of rounded cells.

Following incubation and microscopic examination to confirm CPE, the maintenance medium is decanted and discarded. A volume of 100 ml of Hals medium is added back to each 500 ml roller bottle. Hals medium is basal medium Eagle (BME) with Hank's Salts (Grand Island Biological Co., Grand Island, NY), supplemented with 0.5% lactalbumin hydrolysate (Humko Sheffield, Memphis, Tenn.). The cultures are then frozen at $-50°$ C for 6 hours. After thawing, a binary ethyleneimine (BEI) solution is added to a final concentration of 1% (V/V) to inactivate remaining virus particles. The BEI solution is prepared by adding 2.05 q of 2 bromoethylamine and 0.8 g of sodium hydroxide to 100 ml of water. Inactivation is maintained at 35°–37° C. with constant agitation for up to 2 days incubation. Inactivation is terminated by addition of a cold (4° C.) solution of sodium thiosulfate to give a final concentration of about 0.25% (W/V) of sodium thiosulfate. Merthiolate is added as a preservative to a final concentration of 1:10,000. The final bulk vaccine is prepared by mixing cell culture fluid with maintenance medium and then adding, as an adjuvant, ethylene maleic anhydride to a final concentration of 0.2%. The bulk vaccine typically contains 20% cell culture fluid, 60% maintenance medium and 20% adjuvant solution, by volume. The adjuvant solution is prepared by hydrating a stock solution of ethylene maleic anhydride (EMA 91, Monsanto, St. Louis, Mo.) by addition of 10 N sodium hydroxide. The EMA stock solution contains:

| Chemical | Grams/Liter |
| --- | --- |
| NaCl | 0.5 |
| $KH_2PO_4$ | 0.565 |
| $Na_2HPO_4$ | 0.135 |
| EMA 91 | 10.0 |
| Phenol Red | 0.135 |

EXAMPLE 2

Protection Study

CCV-71, at the 4th passage level on primary dog kidney cells, was passed once on the A 72 cell line (ATCC CRL 1542), divided in appropriate volumes, and stored at $-70°$ C. This virus was designated as the virulent challenge virus and was standardized to contain $10^{5.3}$ $TCID_{50}$ per ml. (Strain CCV-71 is the same as ATCC VR-809.)

The A-72 cell line was obtained from ATCC at passage level 33. At this passage level, the A 72 cells were not sensitive to CCV infection. The cell line was serially propagated for over 100 consecutive passages and used at the 139th to 140th passaqe levels for the CCV propagations and titrations. At this passaqe level, the A-72 cell line was very susceptible to attachment and replication of CCV.

Young, healthy puppies (8–14 weeks old) which did not have ELISA antibody titers to CCV were used in the experiments. They were placed in isolation facilities throughout the duration of the experimental testing.

A total of 20 puppies were each administered two 1 ml doses of vaccine prepared substantially as described in Example 1, subcutaneously, 21 days apart. Five puppies were left nonvaccinated as challenge controls. The 20 vaccinates and 5 controls were bled at the time of vaccination. They were also bled at 21 days post-vaccination (at which time the vaccinates were reinoculated), at 14 days post second vaccination (at which time the puppies were challenged) and at 14 days post-challenge.

Vaccinates and controls were not allowed food for 18 to 24 hours prior to challenge. Challenge was by oral inoculation of 5 ml of the virulent challenge virus $10^{5.3}$ $TCID_{50}$ per ml). At 18 to 24 hours after challenge, the challenged puppies were returned to the normal dietary schedule.

Following challenge, puppies were observed for 14 days for signs or disease or reaction. During the observation period, temperatures were determined and blood samples collected for white blood cell counts. Fecal samples were collected daily for 21 days for determination of coproantibody (intestinal IgA antibody) to CCV.

Following each vaccination, all puppies remained well and normal. Table 4 shows the VN antibody titers of the puppies at pre-vaccination, pre-second vaccination, and pre-challenge. All puppies were VN seronegative at the time of the first vaccination, and remained negative when the second dose was administered. At the time of challenge (two weeks post second vaccination), the VN titers ranged from 0 to 16, with a geometric mean titer of 5. Table 5 illustrates the puppies and bleeding dates as in Table 4, but using the ELISA for determination of antibody titers. The puppies were seronegative at the time of first vaccination and only 7 of these showed antibody responses at the time of second vaccination. At the time of challenge, all puppies showed good ELISA antibody titers.

At 14 days post challenge, the challenged control puppies had a geometric mean ELISA antibody titer of 3880, while the vaccinates geometric mean ELISA antibody titer was $>19,106$ (Table 5). The high humoral antibody titer of the vaccinates is due to vaccination and a good secondary response following challenge and is indicative of protection.

Following challenge, some vaccinated animals exhibited brief or transitory clinical symptoms, ranging from anorexia to vomiting. The challenge control puppies showed signs of anorexia only after challenge. These symptoms were noted generally from days 6 through 10 post-challenge. The challenge control puppies demonstrated more clinical symptoms than did the vaccinated group.

White blood cell counts were monitored daily post-challenge for evaluation of disease. No significant leukopenia was observed in either vaccinated or challenge control puppies. There was a slight leukocytosis in the challenge control puppies beginning at day 9 and continuing through day 13.

TABLE 4

Master Seed Immunogenicity Test
Virus Neutralizing Antibody Titers

| Puppy No. | Virus Neutralizing Antibody Titers Pre-Vac. | Pre-2nd Vac. | Pre-Challenge | Post-Challenge |
|---|---|---|---|---|
| Vaccinates | | | | |
| DE-88 | 0[1] | 0 | 4 | 256 |
| DE-89 | 0 | 0 | 16 | 1024 |
| DE-90 | 0 | 0 | 2 | 256 |
| DE-91 | 0 | 0 | 8 | 512 |
| DE-94 | 0 | 0 | 8 | 1024 |
| DE-95 | 0 | 0 | 8 | 1024 |
| DE-96 | 0 | 0 | 8 | 1024 |
| DE-97 | 0 | 0 | 2 | 128 |
| DE-98 | 0 | 0 | 2 | 256 |
| DE-99 | 0 | 0 | 2 | 256 |
| F-125 | 0 | 0 | 0 | 64 |
| F-126 | 0 | 0 | 0 | 128 |
| F-127 | 0 | 0 | 4 | 64 |
| F-128 | 0 | 0 | 2 | 128 |
| F-129 | 0 | 0 | 4 | 512 |
| F-130 | 0 | 0 | 8 | 2048 |
| F-131 | 0 | 0 | 2 | 1024 |
| F-132 | 0 | 0 | 0 | 512 |
| F-133 | 0 | 0 | 8 | 512 |
| F-134 | 0 | 0 | 16 | 2048 |
| Geometric Mean | 0 | 0 | 5 | 402 |
| Controls | | | | |
| DF-53 | ND[2] | ND | 0 | 64 |
| DF-54 | ND | ND | 0 | 128 |
| DF-55 | ND | ND | 0 | 128 |
| DF-56 | ND | ND | 0 | 512 |
| DF-57 | ND | ND | 0 | 64 |
| Geometric Mean | — | — | 0 | 128 |

[1]Antibody titer expressed as the reciprocal of the highest serum dilution showing complete neutralization.
[2]Not Determined.

TABLE 5

Master Seed Immunogenicity Test
ELISA Neutralizing Antibody Titers

| Puppy No. | ELISA Neutralizing Antibody Titers Pre-Vac. | Pre-2nd Vac. | Pre-Challenge | Post-Challenge |
|---|---|---|---|---|
| Vaccinates | | | | |
| DE-88 | 0[1] | 0 | 640 | >20480 |
| DE-89 | 0 | 80 | 10240 | >20480 |
| DE-90 | 0 | 40 | 5120 | >20480 |
| DE-91 | 0 | 10 | 640 | 20480 |
| DE-94 | 0 | 0 | 320 | >20480 |
| DE-95 | 0 | 0 | 640 | 20480 |
| DE-96 | 0 | 0 | 640 | >20480 |
| DE-97 | 0 | 0 | 640 | 10240 |

TABLE 5-continued

Master Seed Immunogenicity Test
ELISA Neutralizing Antibody Titers

| Puppy No. | ELISA Neutralizing Antibody Titers Pre-Vac. | Pre-2nd Vac. | Pre-Challenge | Post-Challenge |
|---|---|---|---|---|
| DE-98 | 0 | 0 | 1280 | >20480 |
| DE-99 | 0 | 0 | 320 | 20480 |
| F-125 | 0 | 0 | 1280 | >20480 |
| F-126 | 0 | 20 | 640 | >20480 |
| F-127 | 0 | 10 | 160 | >20480 |
| F-128 | 0 | 0 | 640 | 10240 |
| F-129 | 0 | 0 | 320 | >20480 |
| F-130 | 0 | 10 | 1280 | >20480 |
| F-131 | 0 | 20 | 160 | >20480 |
| F-132 | 0 | 0 | 80 | 20480 |
| F-133 | 0 | 0 | 1280 | >20480 |
| F-134 | 0 | 20 | 1280 | >20480 |
| Geometric Mean | 0 | 3 | 715 | >19106 |
| Controls | | | | |
| DF-53 | ND[2] | ND | 0 | 2560 |
| DF-54 | ND | ND | 0 | 5120 |
| DF-55 | ND | ND | 0 | 2560 |
| DF-56 | ND | ND | 0 | 5120 |
| DF-57 | ND | ND | 0 | 5120 |
| Geometric Mean | — | — | 0 | 3880 |

[1]Antibody titer expressed as the reciprocal of the serum dilution where the difference in adsorbance at 410 nm between coronavirus containing microtiter plate wells and cell control containing wells is >0.05.
[2]Not Determined.

Temperature response post challenge was also monitored as a parameter of clinical CCV disease. Temperature response occurred post challenge in both the vaccinates and controls. The relative increase in temperature was more dramatic in the controls than in the vaccinates. The increase in temperature was not high enough to cause concern. The temperature profile in the control puppies appears to be biphasic with a secondary temperature response occurring in 10 days post-challenge. This biphasic temperature profile has been noted before in puppies challenged with virulent CCV. No such biphasic temperature response was noted in the controls.

An ELISA was developed to directly measure the protection afforded in the intestinal tract of vaccinated puppies against infection of the intestinal tract with virulent CCV challenge. Table 6 shows the anti CCV IgA determinations made at daily intervals post-challenge. The anti-CCV IgA remained near or at baseline levels.

The significant increase in anti-CCV IgA in vaccinates beginning at day 7 post-challenge is due to parenteral priming of the intestinal mucosal surfaces with the adjuvanted inactivated CCV vaccine. The oral challenge stimulated the mucosal IgA memory response eliciting a significant anti CCV IgA response in the intestinal tract. This high IgA response is sufficient for protection against infection. There was little to no anti-CCV IgA response in the challenged controls, demonstrating the lack of primed memory cells and lack of protection.

This Example demonstrates that a CCV vaccine comprising the cell associated CCV peplomer is protective against disease caused by infection with CCV.

TABLE 6

Master Seed Immunogencity Test
Fecal Anti-CCV Immunoglobulin A

| Puppy No. | \multicolumn{22}{c}{Days Post Challenge} |
|---|---|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
| Vaccinates | | | | | | | | | | | | | | | | | | | | | | |
| DE-88 | .04 | .03 | .04 | .05 | .01 | .00 | .01 | .01 | .00 | .27 | .38 | .43 | .36 | .56 | .43 | .43 | .33 | .29 | .25 | .26 | .33 | .41 |
| DE-89 | .01 | .09 | .02 | .06 | .00 | .04 | .02 | .07 | .29 | .26 | .52 | .81 | .56 | 1.09 | .78 | .77 | .69 | .66 | .70 | .43 | .65 | .57 |
| DE-90 | .02 | .02 | .01 | .02 | .00 | .04 | .06 | .03 | .06 | .09 | .18 | .22 | .24 | .29 | .28 | .32 | .34 | .12 | .28 | .18 | .18 | .21 |
| DE-91 | .04 | .04 | .01 | .01 | .00 | .04 | .04 | .06 | .14 | .16 | .12 | .18 | .20 | .11 | .12 | .15 | .18 | .20 | .11 | .17 | .15 | .17 |
| DE-94 | .01 | .10 | .14 | .02 | .03 | .03 | .01 | .06 | .07 | .06 | .14 | .14 | .18 | .21 | .10 | .10 | .21 | .28 | .17 | .17 | .14 | .43 |
| DE-95 | .01 | .00 | .01 | .02 | .10 | .01 | .09 | .02 | .05 | .04 | .06 | .32 | .20 | .19 | .22 | .17 | .14 | .19 | .16 | .13 | .10 | .17 |
| DE-96 | .03 | .00 | .01 | .02 | .01 | .00 | .02 | .01 | .12 | .15 | .21 | .14 | .15 | .20 | .26 | .23 | .19 | .28 | .20 | .19 | .18 | .05 |
| DE-97 | .00 | .07 | .00 | .04 | .05 | .02 | .09 | .02 | .08 | .06 | .14 | .14 | .18 | .12 | .13 | .37 | .22 | .15 | .21 | .25 | .14 | .24 |
| DE-98 | .02 | .03 | .02 | .00 | .01 | .00 | .02 | .03 | .08 | .07 | .05 | .04 | .03 | .16 | .18 | .28 | .23 | .11 | .14 | .08 | .07 | .09 |
| DE-99 | .00 | .00 | .00 | .01 | .08 | .04 | .03 | .08 | .11 | .13 | .14 | .16 | .08 | .08 | .12 | .13 | .12 | .10 | .13 | .14 | .03 | .10 |
| F-125 | .03 | .13 | .02 | .02 | .01 | .00 | .02 | .02 | .14 | .19 | .22 | .32 | .37 | .49 | .51 | .47 | .49 | .39 | .39 | .34 | .37 | .29 |
| F-126 | .06 | .00 | .00 | .00 | .04 | .01 | .00 | .02 | .10 | .21 | .26 | .26 | .48 | .37 | .45 | .27 | .24 | .27 | .20 | .20 | .13 | .20 |
| F-127 | .06 | .00 | .00 | .02 | .07 | .06 | .05 | .03 | .20 | .23 | .40 | .33 | .34 | .30 | .34 | .48 | .43 | .43 | .29 | .29 | .37 | .29 |
| F-128 | .00 | .00 | .00 | .01 | .02 | .02 | .01 | .00 | .00 | .03 | .12 | .15 | .17 | .33 | .32 | .30 | .18 | .37 | .19 | .18 | .18 | .22 |
| F-129 | .05 | .02 | .00 | .00 | .01 | .00 | .03 | .05 | .17 | .22 | .25 | .21 | .29 | .52 | .48 | 1.07 | .77 | .54 | .44 | .39 | .13 | .28 |
| F-130 | .17 | .09 | .04 | .05 | .06 | .09 | .01 | .06 | .15 | .48 | .38 | .50 | .76 | .34 | .28 | .35 | .30 | .11 | .24 | .23 | .17 | .04 |
| F-131 | .12 | .00 | .02 | .03 | .05 | .00 | .03 | .04 | .17 | .18 | .32 | .31 | .29 | .43 | .30 | .28 | .36 | .29 | .25 | .30 | .28 | .14 |
| F-132 | .01 | .06 | .02 | .04 | .00 | .04 | .05 | .05 | .05 | .11 | .15 | .17 | .21 | .32 | .17 | .19 | .25 | .07 | .23 | .17 | .32 | .14 |
| F-133 | .20 | .00 | .05 | .02 | .08 | .03 | .02 | .03 | .04 | .11 | .43 | .43 | .45 | .71 | .29 | .61 | .61 | .41 | .19 | .12 | .38 | .47 |
| F-134 | .07 | .00 | .01 | .02 | .01 | .05 | .04 | .05 | .17 | .20 | .27 | .39 | .29 | .26 | .29 | .29 | .12 | .16 | .25 | .25 | .21 | .40 |
| Average | .05 | .05 | .03 | .02 | .03 | .03 | .03 | .04 | .11 | .16 | .24 | .28 | .27 | .35 | .30 | .37 | .32 | .27 | .25 | .22 | .22 | .28 |
| Controls | | | | | | | | | | | | | | | | | | | | | | |
| DF-53 | .044 | .06 | .02 | .03 | .06 | .03 | .02 | .03 | .02 | .01 | .02 | .05 | .05 | .02 | .03 | .13 | .05 | .07 | .06 | .07 | .06 | .04 |
| DF-54 | .03 | .07 | .03 | .02 | .02 | .02 | .01 | .03 | .01 | .02 | .04 | .03 | .04 | .02 | .03 | .13 | .05 | .07 | .06 | .07 | .06 | .04 |
| DF-55 | .02 | .00 | .04 | .01 | .01 | .01 | .05 | .04 | .00 | .01 | .01 | .01 | .05 | .01 | .01 | .04 | .00 | .01 | .01 | .11 | .04 | .20 |
| DF-56 | .02 | .03 | .00 | .01 | .04 | .03 | .03 | .03 | .04 | .02 | .03 | .09 | .01 | .00 | .02 | .03 | .09 | .03 | .12 | .15 | .09 | .04 |
| DF-57 | .02 | .03 | .04 | .02 | .01 | .01 | .00 | .04 | .04 | .00 | .01 | .01 | .01 | .03 | .02 | .08 | .04 | .10 | .07 | .08 | .02 | .04 |
| Average | .03 | .03 | .03 | .02 | .03 | .02 | .02 | .03 | .02 | .01 | .02 | .04 | .03 | .02 | .02 | .06 | .04 | .04 | .05 | .08 | .05 | .10 |

EXAMPLE 3

Combination Vaccine

A bivalent vaccine comprising the CCV vaccine of the invention and a modified live Canine Parvovirus vaccine (6.3 $Log_{10}$ $TCID_{50}$ per dose) was administered to 6 susceptible puppies, 9 to 12 weeks old.

At 3 weeks posts vaccination, the puppies had a geometric mean ELISA antibody titer of 113 to the CCV fraction and a geometric mean VN titer of 912 to the CPV component. At this time the puppies received a second dose of the combination product. At 2 weeks post second vaccination, the CCV geometric mean ELISA antibody titer was 3620 and the CPV geometric mean VN titer was 1448.

A second group of 6 susceptible puppies was vaccinated with a monovalent modified live CPV vaccine (6.3 $Log_{10}$ $TCID_{50}$) The CPV was modified by cell passage. At 3 weeks post vaccination, the puppies had a geometric mean VN antibody titer of 1448 to CPV. At this time, the puppies received a second dose of CPV vaccine. At 2 weeks post-second vaccination, the CPV geometric mean VN titer was 2896. The sera from the different bleedings were monitored for CCV titers and found to be negative for the duration of this test.

Except for one puppy, all puppies showed good responses to CPV. All but that one puppy showed equal responses to the CPV, whether in combination with CCV or as the monovalent product.

This Example demonstrates that the CCV vaccine of the invention can be used in combination with other vaccine components, and, in particular, with a Canine Parvovirus vaccine component.

While the invention and its preferred embodiments are fully disclosed above, it is to be understood that the invention includes all embodiments and modifications coming within the scope of the following claims.

We claim:

1. A vaccine for protecting canine animals from disease caused by infection with Canine Coronavirus (CCV) which comprises an effective amount of CCV peplomer protein and which is free for substantially free of CCV virus externalized during culture of infected cells.

2. The vaccine of claim 1 which is prepared from a cell culture infected with CCV.

3. A vaccine for protecting canine animals from disease caused by infection with Canine Coronavirus (CCV) which comprises an effective amount of CCV peplomer protein in an inactivated culture of cells infected with CCV from which culture the growth medium has been removed.

4. The vaccine of claim 3 which comprises the peplomer protein in an inactivated cell monolayer from which the growth medium has been poured off prior to inactivation.

5. The vaccine of claim 1, 3, 4 or 2 which further comprises an adjuvant.

6. A process for producing a vaccine for protecting animals from disease caused by infection with Canine Coronavirus (CCV) which comprises:
   a. infecting a cell culture with a Multiplicity of Infection (MOI) of CCV of at least 0.2 to 2;
   b. culturing the cells for 6–18 hours;
   c. discarding the spent fluid medium;
   d. disrupting the cells;
   e. collecting the cell-associated peplomer protein from the disrupted cells; and,
   f. combining the cell-associated peplomer with a parenterally acceptable carrier.

7. The process of claim 6 wherein the cells are disrupted in a parenterally acceptable fluid and steps (e) and (f) are thereby combined.

8. The process of claim 6 or 7 which further comprises admixing the carrier containing the cell associated peplomer protein with an adjuvant.

9. The vaccine of claim 1, 3, 4 or 2 which also comprises an effective amount of an antigenic component which is protective against one or more additional pathogenic organisms or viruses.

10. The vaccine of claim 9 in which the cell-associated peplomer protein is prepared by culture of cells infected with CCV.

11. The vaccine of claim 9 in which the additional pathogen is Canine Parvovirus (CPV) and the additional antigenic component is an effective amount of killed CPV or modified live CPV.

12. A method of protecting a canine animal against disease caused by infection by CCV which comprises parenterally administering to the animal the vaccine of claim 1, 3, 4 or 2.

13. A method of protecting a canine animal against disease caused by infections by CCV and from disease caused by infection with one or more additional pathogenic organisms or viruses which comprises parenterally administering to the animal the vaccine of claim 9.

* * * * *